US00PP16068P2

(12) United States Plant Patent
Zaiger et al.

(10) Patent No.: US PP16,068 P2
(45) Date of Patent: Oct. 25, 2005

(54) PEACH TREE 'SWEET HENRY'

(50) Latin Name: *Prunus persica*
Varietal Denomination: Sweet Henry

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 140 days.

(21) Appl. No.: 10/816,301

(22) Filed: Apr. 2, 2004

(51) Int. Cl.[7] ..... A01H 5/00

(52) U.S. Cl. ..... Plt./197

(58) Field of Search ..... Plt./197

*Primary Examiner*—Anne Marie Grunberg

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with an attractive red skin color.
2. Fruit with mild, sweet, sub-acid flavor.
3. Fruit that holds firm on the tree 8 to 10 days after maturity.
4. Fruit with firm, yellow flesh, good handling and shipping qualities.
5. Heavy and regular production of fruit.
6. Vigorous, upright growth of the tree.

1 Drawing Sheet

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach and nectarine trees, which are known to us, and mentioned herein, 'Amparo' Peach (U.S. Plant Pat. No. 6,472), 'O'Henry' Peach (U.S. Plant Pat. No. 2,964), 'June Lady' Peach (U.S. Plant Pat. No. 3,022) and 'May Grand' Nectarine (U.S. Plant Pat. No. 2,794).

STATEMENT REGARDING FEDERALLY SPONSORED RESEARCH AND DEVELOPMENT

Not applicable.

ORIGIN OF THE VARIETY

The new variety of peach tree (*Prunus persica*) was originated by us in our experimental orchard located near Modesto, Calif. as an open pollinated seedling (pollen parent unknown) from seed collected from our proprietary parent labeled 226LK410. The proprietary seedling (226LK410) originated as the second filial generation seedling from the crosses of the following peaches and nectarine. The maternal parent was developed from the cross of a peach of unknown parentage with 'Amparo' Peach (U.S. Plant Pat. No. 6,472). The pollen parent was developed from the crosses of the following varieties, 'O'Henry' Peach (U.S. Plant Pat. No. 2,964), 'June Lady' Peach (U.S. Plant Pat. No. 3,022) and 'May Grand' Nectarine (U.S. Plant Pat. No. 2,794). We planted and maintained a large group of these open pollinated seedlings on their own root system. Under close and careful evaluation we recognized the desirable tree and fruit characteristics of the present late maturing variety and selected it for asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree is of large size, vigorous, upright growth and a productive and regular bearer of large, firm, yellow flesh, clingstone fruit, having a mild, sweet, sub-acid flavor with excellent eating quality. The fruit is further characterized by having an attractive red skin color, being uniform in size throughout the tree and having the ability to hold firm on the tree 8 to 10 days after maturity (shipping ripe). In comparison to its ancestor 'Amparo' Peach (U.S. Plant Pat. No. 6,472) the fruit is larger in size and has a higher degree of attractive skin color and is approximately 50 days later in maturity, and in comparison to 'O'Henry' Peach (U.S. Plant Pat. No. 2,964) the fruit of the new variety ripens approximately 7 days later with a higher degree of attractive red skin color.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color.

Tree:

*Size.*—Large, normal for peach trees. Pruned to 3 to 3.5 meters in height at maturity.

*Vigor.*—Vigorous. Tree growth 1.5 to 2 meters in height the first growing season, varies with fertility, type of soil and cultural practices.

*Form.*—Upright, usually pruned to vase shape.

*Productivity.*—Productive. Normal fruit thinning and spacing necessary. Number of fruit set per tree varies with climatic conditions during blooming period.

*Bearer.*—Regular. Adequate fruit set for 3 consecutive years. No alternate bearing observed.

*Fertility.*—Self fertile.

*Density.*—Medium dense. Pruning to vase shape is desirable to enhance fruit color and keep fruit wood healthy.

*Hardiness.*—Hardy in all stone fruit growing areas of California. Winter chilling requirement approximately 750 hours at or below 45° F.

Trunk:

*Size.*—Large, stocky. Average circumference 49.5 cm at 22.8 cm above ground on a 5 year old tree.

*Texture.*—Medium shaggy, becoming rougher with age.

*Color.*—Varies from 5Y 8/1 to 5Y 7/1.

Branches:

*Size.*—Medium. Average circumference 18.7 cm at 1.2 meters above the ground.

*Surface texture.*—New growth smooth, varies to medium rough with age.

*Lenticels.*—Average number; 49 in a 25.8 square cm section. Average length 2.7 mm. Average width 1.3 mm. Color varies from 7.5YR 6/8 to 7.5YR 5/8.

*Color.*—New growth varies from 7.5Y 5/6 to 10Y 5/8. Old growth varies from 5YR 4/4 to 7.5YR 3/4, becoming darker with age.

Leaves:

*Size.*—Medium to large. Average length 129.8 mm. Average width 35.1 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Average length 12.0 mm. Average width 1.5 mm. Color varies from 7.5Y 6/6 to 7.5Y 5/6. Grooved longitudinally. Glabrous.

*Glands.*—Reniform. Size — small. Average length 0.6 mm. Average diameter 0.5 mm. Number varies from one to three, average number two. Located on base of the leaf blade and upper portion of the petiole. Color varies from 7.5Y 4/6 to 7.5Y 5/6.

*Color.*—Upper surface varies from 5GY 4/4 to 5GY 3/6. Lower surface varies from 5GY 5/4 to 5GY 4/4. Midvein color varies from 7.5Y 6/6 to 7.5Y 6/4.

Flower buds:

*Size.*—Large. Average length 18.5 mm. Average diameter 11.5 mm.

*Hardiness.*—Hardy in all stone fruit growing areas of California.

*Form.*—Conical.

*Pedicel.*—Size — medium. Average length 4.0 mm. Average width 1.5 mm. Color — varies from 2.5GY 6/8 to 5GY 5/8.

*Color.*—Varies from 7.5RP 6/10 to 7.5RP 8/6.

Flowers:

*Size.*—Large, showy. Average height 21.9 mm. Average diameter 42.3 mm.

*Petals.*—Very large. Average length 21.2 mm. Average width 20.1 mm. Number 5, alternately arranged to sepals. Form — orbicular. Margin — sinuate, slightly cupped. Both upper and lower surfaces glabrous. Color varies from 5RP 7/8 to 5RP 8/6.

*Sepals.*—Number — 5, alternately arranged to petals. Shape — triangular. Size — large. Average length 6.6 mm. Average width 4.0 mm. Color — upper surface varies from 5GY 5/8 to 5GY 4/6, glabrous. Lower surface varies from 5GY 6/6 to 5YR 3/2, pubescent.

*Stamens.*—Average number per flower 46. Average filament length 17.5 mm. Filament color varies from 5RP 9/2 to 5RP 5/8. Anther color varies from 5R 3/10 to 7.5R 3/10.

*Pollen.*—Abundant, self fertile. Color varies from 2.5Y 7/10 to 2.5Y 8/12.

*Pistil.*—Normally one. Surface — pubescent. Average length 17.3 mm, compared to stamens, approximately same height. Color varies from 10Y 8/6 to 10Y 8.5/4.

*Fragrance.*—Wanting.

*Blooming period.*—Date of first bloom Feb. 25, 2003. Date of petal fall Mar. 6, 2003. Varies slightly with climatic conditions.

*Color.*—Varies from 5RP 8/6 to 7RP 8/6, varies slightly with age of flower.

*Number flowers per flower bud.*—One.

*Pedicel.*—Medium. Average length 5.0 mm. Average width 1.7 mm. Color varies from 10Y 5/8 to 2.5GY 5/6.

Fruit:

*Maturity when described.*—Firm ripe.

*Date of first picking.*—Aug. 11, 2003.

*Date of last picking.*—Aug. 18, 2003. Varies slightly with climatic conditions.

*Size.*—Large. Average diameter axially 76.7 mm. Average transversely in suture plane 78.0 mm. Average weight 275.5 grams. Average weight varies slightly with fertility of the soil, amount of thinning and climatic conditions.

*Form.*—Globose.

*Suture.*—Shallow, extends from base to apex.

*Ventral surface.*—Nearly smooth, very slightly lipped.

*Apex.*—Varies from rounded to very slight tip.

*Base.*—Slightly retuse.

*Cavity.*—Round to slightly elongated in suture plane. Average depth 9.0 mm. Average diameter 19.1 mm.

Stem:

*Size.*—Medium. Average length 9.4 mm. Average diameter 4.0 mm.

*Color.*—Varies from 10Y 7/6 to 2.5GY 7/6.

Flesh:

*Ripens.*—Evenly.

*Texture.*—Firm, meaty.

*Fibers.*—Few, small and tender.

*Aroma.*—Slight.

*Amydgalin.*—Undetected.

*Eating quality.*—Excellent.

*Flavor.*—Excellent, mild, sweet, sub-acid.

*Juice.*—Moderate amount, enhances flavor.

*Brix.*—Average Brix 12.0°, varies slightly with amount of fruit per tree and climatic conditions.

*Color.*—Yellow, varies from 2.5Y 8/10 to 2.5Y 8.5/10. Pit cavity varies from 7.5R 2/6 to 7.5R 3/10. Slight bleeding from pit cavity into flesh.

Skin:

*Thickness.*—Medium.

*Surface.*—Smooth.

*Down.*—Moderate amount, short in length.

*Tendency to crack.*—None.

*Color.*—Ground color varies from 2.5Y 8.5/8 to 2.5Y 8/8. Nearly overspread with 7.5R 4/8 to 10R 3/6.

*Tenacity.*—Tenacious to flesh.

*Astringency.*—None.

Stone:

*Type.*—Clingstone.

*Size.*—Large. Average length 32.5 mm. Average width 30.2 mm. Average thickness 19.0 mm.

*Form.*—Obovoid.

*Base.*—Flat to slightly rounded.

*Apex.*—Pointed. Average length 1.2 mm.

*Surface.*—Irregularly furrowed toward apex, pitted toward base. Pit cavities vary from round to elongated. Ridges slightly narrow with rough edges.

*Sides.*—Unequal, with one side slightly larger, extending further from suture plane.

*Tendency to split.*—Very slight.

*Color.*—Varies from 10R 3/4 to 2.5YR 3/4 when dry.

Kernal:

*Form.*—Ovate.

*Taste.*—Bitter.

*Viability.*—Viable, embryo developed.

*Size.*—Medium. Average length 18.3 mm. Average width 11.5 mm. Average depth 5.1 mm.

*Skin.*—Color varies from 5YR 4/6 to 5YR 4/8 when dry.

Use: Dessert. Market — local and long distance.

Keeping quality: Good, held firm in cold storage at 38° to 42° F. for 21 days without internal breakdown or appreciable loss of flavor.

Shipping quality: Minimal skin scarring or bruising of flesh during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance of susceptibility has been observed. Any variety observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of peach tree, substantially as illustrated and described, characterized by its large size, vigorous, upright growth and being a productive and regular bearer of large, yellow flesh, clingstone fruit with a mild, sweet, sub-acid flavor and excellent eating quality; the fruit is further characterized by its attractive red skin color, its firm flesh with good storage and shipping quality and, in comparison to 'O'Henry' Peach (U.S. Plant Pat. No. 2,964), the fruit of the new variety has a higher degree of attractive red skin color and is approximately 7 days later in maturity.

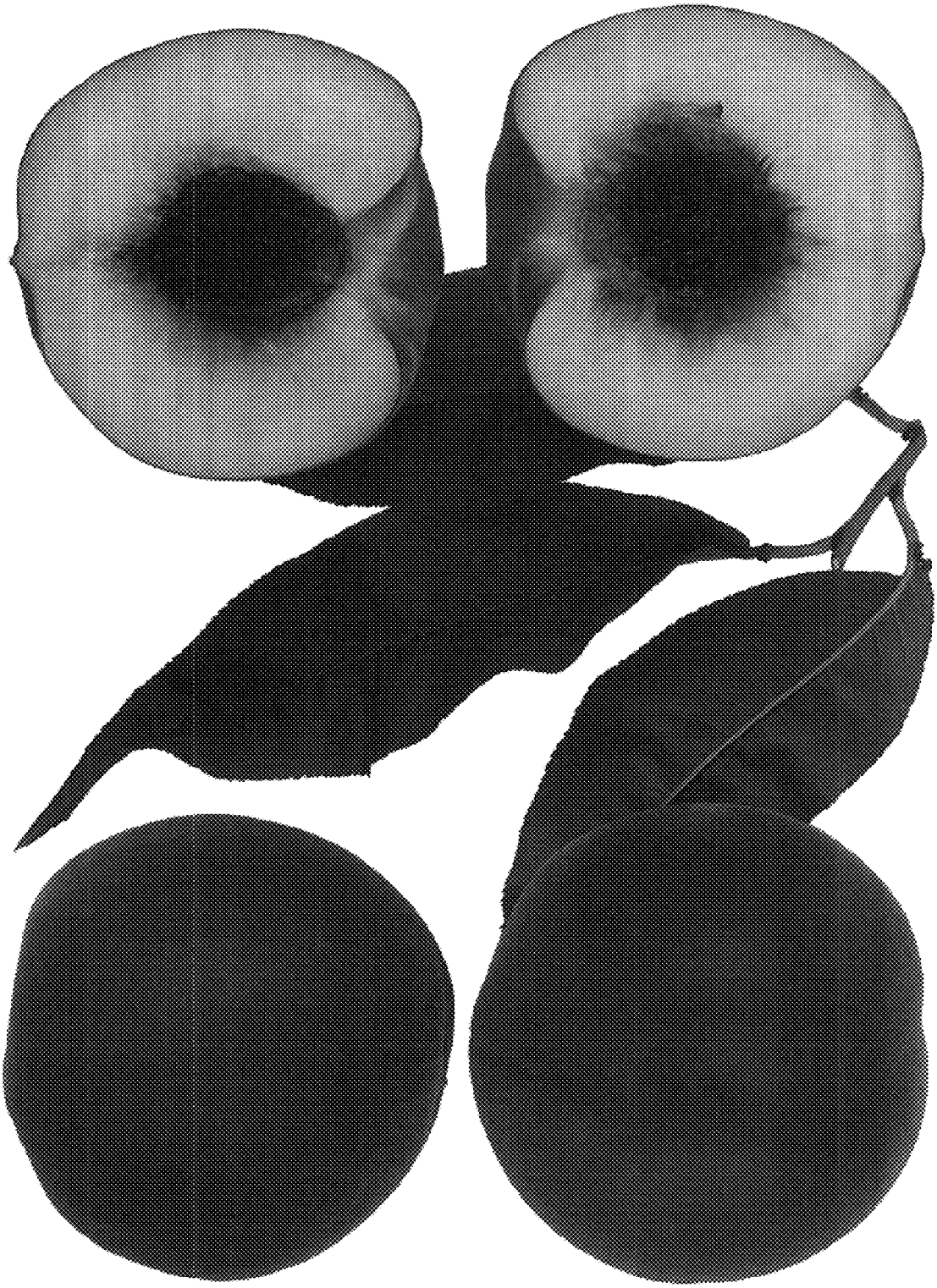

* * * * *